United States Patent [19]

Mettenleiter

[11] Patent Number: 5,738,854
[45] Date of Patent: Apr. 14, 1998

[54] PSEUDORABIES VIRUS VACCINE

[75] Inventor: Thomas Christoph Mettenleiter, Tuebingen, Germany

[73] Assignee: Akzo Nobel N.V., Arnhem, Netherlands

[21] Appl. No.: 681,129

[22] Filed: Jul. 22, 1996

Related U.S. Application Data

[63] Continuation of Ser. No. 244,446, filed as PCT/EP93/02738 Oct. 6, 1993, abandoned.

[30] Foreign Application Priority Data

Oct. 6, 1992 [NL] Netherlands ............... 922030796

[51] Int. Cl.$^6$ .................. A61K 39/245; C12N 5/10; C12N 7/04; C12N 15/38
[52] U.S. Cl. .................. 424/205.1; 424/199.1; 424/229.1; 435/172.1; 435/172.3; 435/235.1; 435/320.1; 435/325; 435/236; 435/252.3; 536/23.72; 935/65
[58] Field of Search ............... 435/235.1, 172.3, 435/252.3, 172.1, 320.1, 236, 325; 536/23.72; 424/199.1, 205.1, 229.1; 935/65

[56] References Cited

U.S. PATENT DOCUMENTS 4,650,677  3/1987  Roerink .................. 424/229.1

FOREIGN PATENT DOCUMENTS

| 0 256 677 WOA 87 | 2/1988 | European Pat. Off. |
| 00862 WOA 91 | 2/1987 | WIPO. |
| 02795 WOA 92 | 3/1991 | WIPO. |
| 15328 | 9/1992 | WIPO. |

OTHER PUBLICATIONS

Lomniczi, B.A. et al. 1984. Journal of Virology, vol. 52, pp. 198–205.
Lomniczi, B.A. et al. 1987. Journal of Virology, vol. 61, pp. 796–801.
Ladin, B.F. et al. 1982. Virology, vol. 116, pp. 544–561.
De Wind, N. et al. Journal of Virology, vol. 66, pp. 7096–7103 Dec. 1992.
Klupp, B.G. et al. Dec. 1992. Virology, vol. 191, pp. 900–908.
Mettenleiter, T.C. et al. Journal of Virology, vol. 62, pp. 2712–2717 1988.

*Primary Examiner*—Mary E. Mosher
*Attorney, Agent, or Firm*—Mary E. Gormley

[57] ABSTRACT

The present invention is concerned with the preparation of a pseudorabies virus (PRV) mutant, formed by a mutation in open reading frame 1 of the BamHI fragment 4. The invention also relates to a PRV mutant containing a heterologous gone encoding an antigen of a porcine pathogen, which is incorporated into ORF1 of the BamHI fragment 4 nucleic acid. Such a PRV mutant can be used as a vector vaccine to induce an immune response after infection in an appropriate host animal. In addition, the PRV mutant is suitable for distinguishing between animals infected by the vaccine virus and animals infected by naturally-occurring viruses.

10 Claims, 1 Drawing Sheet

5,738,854

PSEUDORABIES VIRUS VACCINE

This is a continuation of application Ser. No. 08/244,446, filed as PCT/EP93/02738 Oct. 6, 1993, now abandoned.

FIELD OF THE INVENTION

The present invention is concerned with a pseudorabies virus (PrV) mutant, a recombinant DNA molecule comprising PrV DNA, a host cell transformed with said recombinant DNA molecule, a cell culture infected with the mutant, a vaccine derived from the PrV mutant, as well as a method to distinguish whether an animal has been vaccinated or is infected with naturally-occurring Pseudorabies virus.

BACKGROUND OF THE INVENTION

Pseudorabies virus is a member of the herpes virus group. It is the causative agent of Aujeszky's disease which induces serious economic losses especially among piglets in swine breeding farms and leads to latent infection in older animals. The predominant visible feature of PrV infection is intense pruritus generally resulting in host mutilation of the involved area. Violent excitement, fits and paralysis, all symptoms of encephalomyelitis, precede death which usually occurs within a few days following onset of clinical signs.

The research and development trend among traditional vaccine manufacturers has generally emphasized research leading to vaccines that are based upon virus subunits rather than live viruses. This departure from modified live virus vaccines is partly due to the recognized safety of such subunit vaccines because their unlikelihood to contain infectious live viruses. Another reason for developing a subunit vaccine has been to allow for the development of a diagnostic test that would accompany the vaccine and would differentiate vaccinated from infected animals.

Subunit vaccines have also their limitations. They contain a limited number of viral antigens compared to those produced by live viruses. This paucity of antigens produces a weak immune response of short duration in the vaccinated animal. This, however, is partly advantageous because it allows to discern vaccinated animals from infected animals. Vaccination only will stimulate production of antibodies to the limited spectrum of antigens present in the vaccine. By sampling the serum of the animal, it is possible to show that the vaccinated animal has antibodies only to the antigens contained in the vaccine while an animal infected with the wild-type virus would have antibodies against a wider range of antigens.

Live modified virus vaccines have the advantage that they comprise more antigens and that thus a stronger immune response can be obtained. The chances are that uncontrolled mutations occur during passaging, resulting in populations of virus particles which are heterogeneous in virulence and immunizing properties. More importantly, it is well known that such traditional attenuated viruses can revert to virulence resulting in disease of the vaccinated animals and the possible spread of the pathogen to other animals.

The approach of deleting a gene to attenuate a virus coupled with a diagnostic tool for that gene, provides a vaccine that can be differentiated from any of the currently used PrV vaccines and from naturally-occurring PrV.

Herpes viruses of the PrV type contain in their core a double-stranded DNA molecule with a molecular weight of about 90×10⁶ daltons (D), separated by inverted repeats into a long and a short unique region—UL and US, respectively (Sheldric, P. and N. Berthelot, 1975. Inverted repetitions in the chromosome of herpes simplex virus. Cold Spring Harbor Symp. Quant. Biol. 39:667–678).

Sequencing, mapping of mRNA, and analyses of mutants have shown that the herpes virus genome encodes a minimum of 75 open reading frames (ORFs), of which 69 map in the UL and US sequences (McGeoch, D. J., M. A. Dalrymple, A. J. Davison, A. Dolan, M. C. Frame, D. McNab, L. J. Perry, J. E. Scott and P. Taylor, 1988. The complete DNA sequence of the long unique region in the genome of herpes simplex virus type 1. J. Gen. Virol. 69:1531–1574; Wagner, E. K., 1984. Individual HSV transcripts. Characterization of specific genes, p. 45–104. In: B. Roizman (ed.), The Herpesviruses, vol. 3, Plenum Press, New York.).

The genome of the herpes viruses is commonly referred to in terms of restriction enzyme fragments. For pseudorabies virus recently the sequence of the Bam HI fragments 11 and 16 has been published (Klupp, B. G. and T. C. Mettenleiter, 1991. Sequence and expression of the glycoprotein gH gene of Pseudorabies Virus. Virology 182:732–741).

Recently a US patent has been issued (U.S. Pat. No. 5,037,742) which discloses the use of PrV as a vector for foreign genes. The gIII-region is specifically used for this purpose. In U.S. Pat. No. 5,047,237 a virus vaccine has been disclosed which contains a mutation in the gpX-sequence. In EP 0 141 458 gI⁻ mutants have been described.

SUMMARY OF THE INVENTION

The object of the invention is to provide a PrV mutant which can be used for the preparation of a modified live vaccine, which can be given without the risk of inoculating animals with inadequately attenuated pathogenic microorganisms. In addition, the risk that attenuated pathogens may revert to a virulent state resulting in disease of the inoculated animals and the possible spread of pathogen to other animals, can be reduced by use of a mutant virus.

Furthermore, the PrV mutant offers the possibility of a multivalent vaccine without the risk of adverse mutual interference of different antigenic components.

Another object of the present invention is to provide a PrV vaccine virus which is distinguishable from any field strain. It is important to discriminate between animals vaccinated with a PrV vaccine and those infected with a wild type virus so as to be able to take appropriate measures to reduce spreading of a virulent virus.

DETAILED DESCRIPTION OF THE INVENTION

Figure 1:
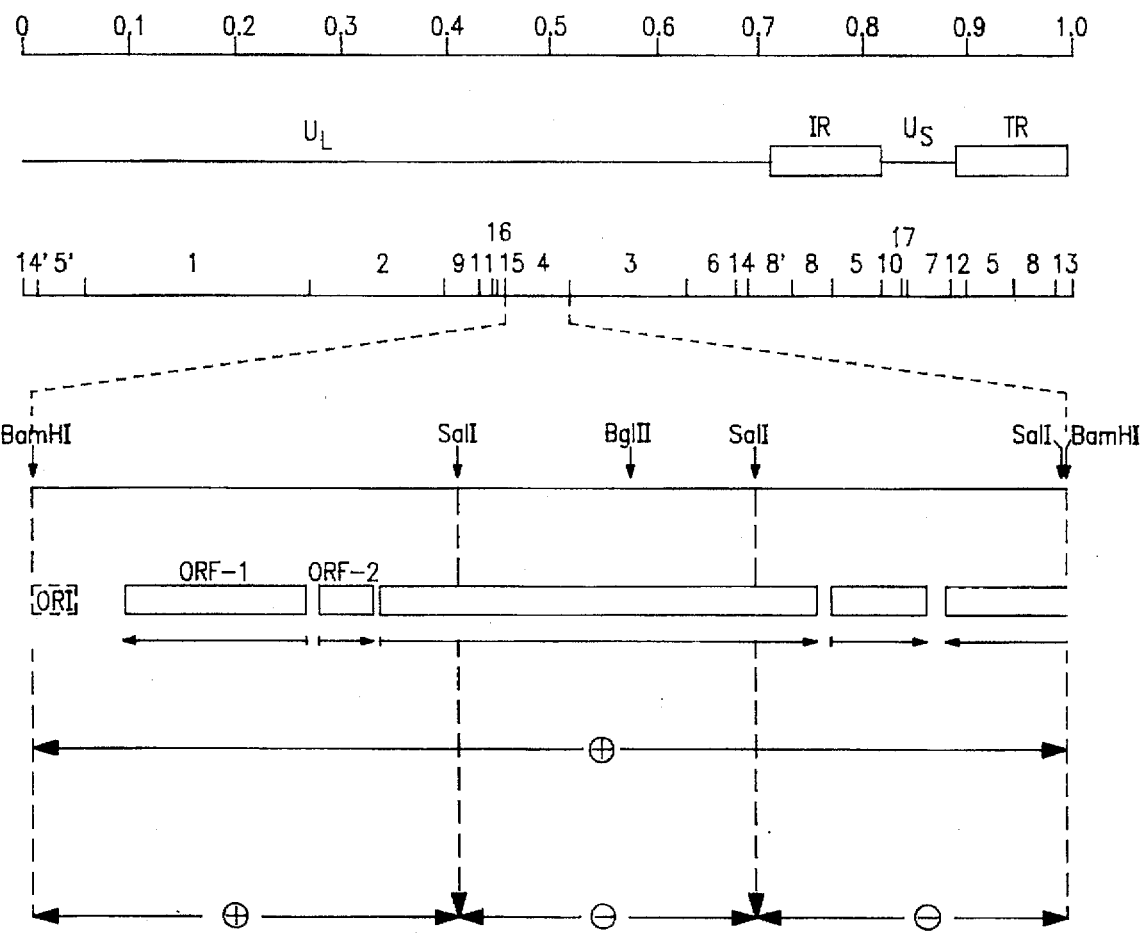
FIG. 1 diagrams the marker rescue experiments with subfragments of BamHI-4 using SalI-subfragments of 2.7 kbp, 2.9 kbp and BamHI/SalI-subfragment of 3.8 kbp. The location of the BamHI restriction sites is indicated in the middle part of the Figure. The location of the ORFs within the BamHI-4 fragment is indicated by the open bars. Results (+or −) of the marker rescue experiments are summarized in the lower part of the Figure.

Both objects are met by providing a PrV mutant comprising a mutation obtained by recombinant DNA techniques in a part of the PrV genome which spans the region comprising the DNA sequences of the open reading frame (ORF) encoding the polypeptide as shown in SEQ ID NO:2.

The term "recombinant DNA techniques" used herein refers to in vitro techniques to produce DNA molecules containing novel combinations of (coding) sequences or altered sequences, and the insertion of these into vectors that can be used for their incorporation into host organisms or cells in which they are capable of continued propagation of the modified sequences.

The term "polypeptide" refers to a molecular chain of amino acids, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

A mutation is understood to be a change of the genetic information by recombinant DNA techniques in the above-mentioned region with respect to the genetic information present in this region of the genome of naturally occurring PrV.

The mutation is, in particular, a nucleic acid substitution, deletion, insertion or inversion, or a combination thereof resulting in a PrV mutant which fails to produce the antigenic or functional polypeptide, shown in SEQ ID NO:2, or in a PrV mutant which contains an inserted heterologous nucleic sequence. The mutation may result also in the production of a polypeptide deviating from the above-mentioned polypeptide of SEQ ID NO:2 displaying altered antigenic or functional properties.

Most preferably the mutation is a deletion and/or an insertion and/or one or more nucleotide substitutions.

The preferred substitution herein is a combination of substitutions such that the codon encoding His at position 37 is changed to a codon encoding Arg, the codon encoding Glu at position 355 is changed to a codon encoding Asp, and the codon encoding Val at position 375 is changed to a codon encoding Ala.

Also a mutation can occur in the control elements for the ORF localized in the intergenic sequence, which may result in a failure of the expression of the polypeptide.

The deletion in the genome of the PrV mutant may comprise a whole ORF.

PrV mutants according to the invention can also be obtained by inserting a nucleic acid sequence into the genome thereby preventing or altering the expression of the polypeptide shown in SEQ ID NO:2.

The BamHI 4 fragment of the PrV virus comprises the nucleic acid sequence spanning 9382 nucleotide base pairs (GenBank Data Library Accession No. L00676). This sequence comprises inter alia two open reading frames:

a. ORF-1 localized between basepair no. 760 and base pair no. 2333, which in opposite direction codes for the polypeptide shown in SEQ ID NO:2, having 525 amino acids;

b. ORF-2 localized between base pair no. 2440 and base pair no. 2921, which in this direction codes for a polypeptide, having 161 amino acids.

The (insertion-)region referred to in the present invention (SEQ ID NO:1) has not been identified previously within the PRV genome. Surprisingly, it has been found that a mutation is allowable in this region without disrupting essential functions of the PrV.

In particular it has been found herein that nucleotide substitution $A_{110}$ to $G_{110}$, $A_{1065}$ to $C_{1065}$ and $T_{1124}$ to $C_{1124}$ resulting in a change of the respective codons results in the expression of a polypeptide having functional characteristics deviating from those of the polypeptide shown in SEQ ID NO:2 such that the PrV mutant thus obtained is less virulent than the parent virus.

The above-mentioned nucleotide substitution results in 3 amino acid exchanges in the deduced ORF gene product: His at position 37 is substituted by Arg, Glu at position 355 is substituted by Asp and Val at position 375 is substituted by Ala.

Unexpectedly, it has been found that the introduction of a mutation into the region defined above in particular the substitution outlined above significantly reduces the virulence of the live PrV mutant without affecting the protective properties of the PrV mutant. This finding has offered the possibility to obtain an attenuated PrV mutant, e.g. by introducing a deletion or insertion or substitution into the region defined above.

In a preferred embodiment of the invention a PrV mutant has a mutation in the part of the PrV genome having the nucleic acid sequence as shown in SEQ ID NO:1.

It will be understood that for the DNA sequence coding for the polypeptide of SEQ ID NO:2 natural variations can exist between individual Pseudorabies viruses. These variations may result in a change in one or more nucleotides in the ORF which, however, will still encode functional polypeptides.

Moreover, the possibility exists to use genetic engineering technology to bring about above-mentioned variations resulting in a DNA sequence related to the sequence shown in SEQ ID NO:1 which still encodes functional polypeptide. It is clear that PrV mutants comprising a mutation in such a corresponding nucleic acid sequence are also included within the scope of the invention.

Although the PrV mutant according to the invention is derived from the strain Ka, any PrV strain can be used to prepare the PrV mutant, such as NIA-3, RICE, 75V19 or Phylaxia.

PrV mutants can be provided with an insertion in the DNA sequence defined herein.

In one aspect of the invention such an insert is merely meant to prohibit or alter the expression of the polypeptide shown in SEQ ID NO:2. This can for instance be done by insertion of a number of base pairs which is not divisable by three, thereby shifting the reading frame, or by inserting a sequence containing a stop codon, or by inserting a nonsense sequence.

Alternatively, the insert comprises a heterologous nucleic acid sequence encoding a polypeptide.

The prerequisite for such a useful recombinant PrV mutant is that the heterologous nucleic acid sequence is incorporated in a permissive position or region of the genomic PrV sequence, i.e. a position or region which can be used for the incorporation of a heterologous sequence without disrupting essential functions of PrV such as those necessary for infection or replication. Such a region is called an insertion-region.

The term "recombinant PrV mutant" as used herein denotes infective virus which has been genetically modified by incorporation into the virus genome of a heterologous nucleic acid sequence, i.e. DNA which comprises a nucleic acid sequence not identical to the nucleic acid sequence of a gene naturally present in PrV.

On infection of a cell by the recombinant PrV mutant, it may express the heterologous gene in the form of a heterologous polypeptide.

The insertion-region referred to in the present invention has not been identified previously within the PrV genome. Surprisingly, it has been found that a mutation such as the incorporation of heterologous DNA is allowable in this region without disrupting essential functions of the PrV.

In summary, the insertion-region essentially defined above characterizes the localization of a region within the PrV genome which can be used to introduce a deletion or to incorporate a heterologous nucleic acid sequence, if desired after deleting DNA sequences from this region, or can be used to introduce other mutations in said region.

The heterologous nucleic acid sequence to be incorporated into the PRV genome according to the present invention can be derived from any source, e.g. viral, prokaryotic, eukaryotic or synthetic. Said heterologous nucleic acid sequence can be derived from a pathogen, preferably a porcine pathogen, which after insertion into the PrV genome can be applied to induce immunity against disease.

Preferably nucleic acid sequences encoding a polypeptide of parvovirus, enteropathogenic *Escherichia coli*, foot and mouth disease virus, *Bordetella bronchiseptica, Mycoplasma hyopneumoniae, Pasteurella multocida* or *Streptococcus suis* are contemplated for incorporation into the insertion-region of the PRV genome.

Furthermore, heteronucleic acid sequences encoding polypeptides for pharmaceutical or diagnostic applications, in particular immuno-modulators such as lymphokines, interferons or cytokines, or marker enzymes as β-galactosidase or superoxide-dismutase may be incorporated into said insertion-region.

An essential requirement for the expression of the heterologous nucleic acid sequence in a recombinant PrV mutant is an adequate promoter operably linked to the heterologous nucleic acid sequence. It is obvious to those skilled in the art that the choice of a promoter extends to any eukaryotic, prokaryotic or viral promoter capable of directing gene transcription in cells infected by the recombinant PrV, e.g. promoters of the retroviral long terminal repeat (Gorman et al., Proc. Natl. Acad. Sci. USA 79, 6777–6781, 1982), the SV40 promoter (Mulligan and Berg, Science 209, 1422–1427, 1980) or the cytomegalovirus immediate early promoter (Schaffner et al., Cell 41, 521–530, 1985).

The technique of in vivo homologous recombination can be used to introduce a nucleic acid sequence carrying the mutated sequence into the PrV genome.

The first step of this technique includes the construction of a recombinant DNA molecule for recombination with PrV genomic DNA. Such a recombinant DNA molecule may be derived from any suitable plasmid, cosmid or phage, plasmids being most preferred, and comprises a fragment of PrV DNA containing DNA of the part of the PrV genome as defined above.

A mutation can be introduced in this fragment by deletion or by insertion of a heterologous nucleic acid sequence, optionally in combination with controlling sequences.

The DNA sequence of the part of the PrV genome as defined above preferably is flanked by PrV nucleic acid sequences which should be of appropriate length, e.g. 50–3000 bp, as to allow in vivo homologous recombination with the viral PrV genome to occur.

The recombinant DNA molecule obtained in this way is suitable for introducing the mutation into the PrV genome.

If desired, a recombinant DNA molecule can be made which contains two or more different heterologous nucleic acid sequences derived from the same or different pathogens, said sequences being incorporated into insertion-region sequences which are flanked by PrV nucleic acid sequences. Such a recombinant DNA molecule can be employed to produce recombinant PrV which expresses two or more different antigenic polypeptides to provide a multivalent vaccine.

Next, cells, e.g. swine kidney cells or VERO cells, can be transfected with PrV DNA or infected with a wild type PrV in the presence of the recombinant DNA molecule as described above whereby recombination occurs between the sequences in the recombinant DNA molecule and the corresponding sequences in the PrV genome.

Recombination can also be brought about by co-transfecting the cells with a nucleic acid sequence containing the mutation sequence flanked by appropriate flanking PrV sequences without plasmid sequences. Recombinant viral progeny is thereafter produced in cell culture and can be selected for example genotypically or phenotypically, e.g. by hybridization or by detecting enzyme activity encoded by a gene co-integrated along with nucleic acid sequence comprising the mutation. Another possibility is the detection of the absence of the polypeptide for which the nucleic acid sequence in which the mutation was localized was coding. In the same way the presence of the polypeptide coded for by an inserted heterologous nucleic acid sequence can be detected. Recombinant virus can also be selected positively based on resistance to compounds such as neomycin, gentamycin or mycophenolic acid. The selected recombinant PrV can be cultured on a large scale in cell culture after which recombinant PrV containing material or heterologous polypeptides expressed by said PrV can be collected thereof.

Host cells transformed with a recombinant DNA molecule as defined above also form part of the invention.

Also another part of the invention is formed by cell cultures infected with PrV mutants according to the invention.

A live PrV mutant according to the present invention can be used to vaccinate animals, particularly pigs. When vaccination with a PrV mutant in which the mutation is a deletion, preferably no expression of the PrV polypeptide as shown in SEQ ID NO:2 is established while still replication of the PrV mutant in the inoculated host takes place.

When vaccination is accomplished with a PrV mutant expressing one or more different heterologous polypeptides of specific pathogens it is preferably followed by replication of the recombinant PrV within the inoculated host, expressing in vivo the heterologous polypeptide along with the PrV polypeptides. The polypeptides expressed in the inoculated host will then elicit an immune response against both PrV and the specific pathogen. If the heterologous polypeptide derived from the specific pathogen can stimulate a protective immune response, then the animal inoculated with a recombinant PrV mutant according to the invention will be immune to subsequent infection by that pathogen as well as to infection by PrV. Thus, a heterologous nucleic acid sequence incorporated into the insertion-region of the PrV genome according to the invention may be continuously expressed in vivo, providing a solid, safe and long-lasting immunity to a pathogen.

A PrV mutant according to the invention containing and expressing one or more different heterologous polypeptides can serve as a monovalent or multivalent vaccine.

For the preparation of a live vaccine the PrV mutant according to the present invention can be grown on a cell culture of porcine origin or on VERO cells. The viruses thus grown can be harvested by collecting the tissue cell culture fluids and/or cells. The live vaccine may be prepared in the form of a suspension or may be lyophilized.

In addition to an immunogenically effective amount of the PrV mutant the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol F(R) or Marcol 52(R), saponins or vitamin-E solubilisate).

The useful dosage to be administered will vary depending on the age, weight and mode of administration. A suitable dosage can be for example about $10^2$–$10^7$ pfu/animal.

An PrV mutant according to the invention can also be used to prepare an inactivated vaccine.

For administration to animals, the PrV mutant according to the presentation can be given inter alia intranasally, intradermally, subcutaneously or intramuscularly.

It is a further object of the present invention to produce subunit vaccines, pharmaceutical and diagnostic preparations comprising a heterologous polypeptide expressed by the PrV mutant according to the invention. This can be achieved by culturing cells infected with said PrV mutant under conditions that promote expression of the heterologous polypeptide. The heterologous polypeptide may then be purified with conventional techniques to a certain extent depending on its intended use and processed further into a preparation with immunizing, therapeutic or diagnostic activity.

The above described active immunization against specific pathogens will be applied as a protective treatment in healthy animals. It goes without saying that animals already infected with a specific pathogen can be treated with antiserum comprising antibodies evoked by a PrV mutant according to the invention comprising a heterologous gene derived from the specific pathogen encoding an antigenic polypeptide. Antiserum directed against a PrV mutant according to the invention can be prepared by immunizing animals, for example pigs, with an effective amount of said PrV mutant in order to elicit an appropriate immune response. Thereafter the animals are bled and antiserum can be prepared.

The invention also provides a method for distinguishing an animal vaccinated with a vaccine of the present invention from an animal infected with naturally occurring PrV. This method comprises analyzing a body fluid of the animal for the presence of antigens normally expressed in and circulating in the body fluid of an animal infected with a naturally-occurring PrV, identifying antigens which are present in the body fluid and correlating said antigens with antigens expressed in and circulating in the body fluid of an animal infected with a pseudorabies virus mutant of the invention. The presence of antigens which are normally expressed in the animal by a naturally-occurring PrV is indicative for infection with PrV, while the presence of the same antigens with the exception of those no longer included in the PrV mutant of the invention is indicative of an animal vaccinated with the vaccine of the invention and not infected with a naturally-occurring pseudorabies virus.

Determining the presence and identification of the antigens can be done directly by the detection of the antigens in the body fluid or indirectly by the detection of antibodies in the body fluid which are specific for the antigens.

More specifically the discrimination between animals vaccinated with a vaccine which comprises the PrV mutant of the invention and animals infected by naturally occurring viruses can be accomplished by analyzing a body fluid for the presence of the polypeptide shown in SEQ ID NO:2 and at least one other antigen normally expressed in an animal both by the PrV mutant and by a naturally-occurring PrV. Antigens or antibodies which are present in the body fluid are identified and the presence or absence of said antigens or polypeptides is determined. The presence of antigens which are normally expressed in an animal infected by a naturally-occurring virus or antibodies against such antigens and the absence of the polypeptide shown in SEQ ID NO:2 or antibodies against such polypeptides would be indicative of an animal vaccinated with the vaccine of the invention and not infected with naturally-occurring PrV.

Another aspect of the invention is a test kit for distinguishing the PrV mutant of the invention from naturally-occurring PrV mutants in the body fluid of an animal. Such a test kit comprises a compound suitable for the detection of the polypeptide shown in SEQ ID NO:2, or antibodies against it, and a compound suitable for the detection of an antigen expressed by both the PrV mutant according to the invention and naturally-occurring PrV strains, or antibodies against said antigen.

Another test can be performed to determine if an animal is infected by a naturally-occurring PrV. In this case only a test on the presence of antigens from or antibodies against the polypeptide shown in SEQ ID NO:2 can show if an animal has been infected by a naturally-occurring PrV.

Accordingly a test kit comprising only the test on the presence of antigens from or antibodies against the polypeptide shown in SEQ ID NO:2 forms part of the invention.

EXAMPLES

1. Virus and Cell Culture

The virulent PRV strain Ka and mutant PRV strains were propagated and plaque-purified in Madin Darby bovine kidney cells (MDBK, ATCC CCL 221) or in SK-6 porcine kidney cells.

The cells were maintained in Eagle minimal essential medium (MEM) with 10% newborn calf serum (Boehringer, Mannheim, FRG) and 100 units/ml penicillin and 100 µg/ml streptomycin. For growth of virus also BHK (baby hamster kidney) cells were used in Dulbecco modified minimal essential medium (DMEM). Virions were purified from the supernatant of infected cells (ca. 5 pfu/cell) by differential centrifugation and velocity sedimentation through 12 to 52% (w/v) sucrose gradient as recently described (Lukacs et al., 1985).

The virion band was aspirated, diluted with 0.2M Tris-HCl, 5 mM EDTA, 0.15M NaCl, and concentrated by pelleting in a SW27 rotor (Beckman) at 25,000 RPM, 4° C. for one hour.

2. Subcloning and Sequence Analysis

Bam HI fragment 4 of the wildtype pseudorabies virus strain Ka was subcloned as a 3.8 kb Bam HI/Sal I fragment, a 2.7 kb Sal I fragment and a 2.9 kb Sal I fragment into a pBR322 derivative into which a multiple cloning site originating from bacteriophage M13mp18 had been introduced. The extreme left and right termini of the whole Bam HI-4 fragment were sequenced. For further sequencing a nested set of overlapping deletion subclones were prepared by exonuclease III/nuclease S1 digestion (Henikoff, S., 1986. Unidirectional digestion with exonuclease III created targeted breakpoints for DNA sequencing. Gene 28:351–359) using a commercially available kit (Pharmacia, Freiburg, Germany). DNA sequence analysis was performed by the dideoxy chain termination method (Sanger, F., Nicklen, S. and Coulson, A. R., 1977. DNA sequencing with chain terminating inhibitors. Proc. Natl. Acad. Sci. USA 74:5463–5467) on double-strand plasmid DNA (Hattori, M. and Sakaki, Y., 1986. Dideoxy sequencing method using denatured plasmid templates. Anal. Biochem. 152:232–238) using pBR322-specific oligonucleotides as primers (New England Biolabs). 7-deaza-2'-deoxy-GTP was used in stead of dGTP in sequencing reactions to minimize band compression (Mizusawa S., Nishimura, S. and Seela, F., 1986. Improvement of dideoxy chain termination method of DNA sequencing by use of deoxy-7-deazaguanosine triphosphate in place of dGTP. Nucleic Acids Res. 14, 1319–1324) resulting from the high G+C content of pseudorabies virus DNA. Sequencing products were labelled with 35S-dATP (Amersham-Buchler, Braunschweig, Germany) and electrophoretically separated fragments were visualized by autoradiography. Sequences of both strands of the viral DNA were determined at least twice on independent clones. Orientation of Bam HI fragment 4 relative to Bam HI-15 was determined by partial sequencing of a Sal I-fragment containing the Bam HI-15 junction.

Sequences obtained were compiled using the University of Wisconsin Genetics Computer Group software package (Devereux, J., Haeberli, P. and Smithies, O., 1984. A comprehensive set of sequence analysis for the VAX. Nucleic Acids Res. 12:387–395) in VAX/VMS version 7.1. It was found that the sequence contained two open reading frames. A first ORF (SEQ ID NO:1), ORF-1, can be found from base pair no. 760 to base pair no. 2333. The start codon is localized at base pair 2333, indicating a transcription direction opposite to the second ORF, ORF-2, which can be found from base pair no. 2440 to base pair no. 2921.

The intergenic sequence between the two ORF's comprises an AT-rich sequence, which probably functions as a control element.

3. Determination of Virulence Marker.

The non virulent PRV Bartha strain has 3 different lesions in its genome. Firstly, a deletion in the US region influencing the expression of the glycoproteins gI and gp63 (Lomniczi et al. J.Virol. 49, 970–979 (1984)). Secondly, a mutation in the nonessential gIII glycoprotein (Mettenleiter et al. J.Virol. 62, 2712–2717 (1988)). Thirdly, an effect in the BamHI-4 fragment that was not defined yet (Lomniczi et al., J.Virol. 61, 796–801 (1987)). To define the exact nature of this defect the BamHI-4 fragment of both the Bartha and the wildtype Kaplan strain were sequenced. A 3.8 kb BamHI/salI, a 2.7 kb SalI/SalI, and a 2.9 SalI/SalI subfragment of the BamHI-4 fragment were subcloned in pBR322. Firstly, the left and the right termini of the BamHI-4 fragment were sequenced. Secondly, a overlapping nested set of deletion subclones was prepared by exonucleaseIII/nuclease S1 digestion using a commercially available kit (Pharmacia, Freiburg, Germany). Then both strands of the viral DNA were sequenced twice on independent clones. The sequences overlapping the SalI sites were determined by using nested deletion subclones from the complete BamHI-4 fragment. DNA sequence analyses was performed by the dideoxy chain termination method using pBR322 specific oligonucleotides as primers. Sequence comparison of the 3.8 BamHI/SalI subfragment of the Bartha strain and the wildtype Kaplan strain revealed 7 nucleotide changes in the region of the ORF (SEQ ID NO:1), 3 of which resulted in an amino acid change in the ORF (Table 1).

TABLE 1

| nucleotide position | virulent | attenuated | amino acid position | virulent | attenuated |
|---|---|---|---|---|---|
| 110 | A | G | 37 | His | Arg |
| 1065 | A | C | 355 | Glu | Asp |
| 1124 | T | C | 375 | Val | Ala |

No amino acid changes could be found in the ORF-2, the N-terminal part of the subsequent ORF or in the ori consensus. To determine if the reduced virulence of the Bartha strain is caused by these amino acid sequence changes, the ORF of the Bartha strain corresponding to the ORF defined herein was replaced by this ORF (SEQ ID NO:1) of the Kaplan strain. In this marker rescue experiment a Bartha strain was used where the gIII as well as the gI/gp63- defects had already been restored. The complete 3.8 kb BamHI/SalI fragment of the Kaplan strain (without the 7 mutations) was subcloned in pBR322. This fragment was exchanged with the BamHI/SalI fragment of the Bartha strain by cotransfection of the 3.8 kb fragment with the gIII-gI/gp63 restored Bartha mutant. Bartha clones with the 3.8 kb Kaplan fragment were selected and further purified by three rounds of plaque purification.

An animal experiment with the Bartha strain, the Bartha strain with the restored gIII and gI/gp63 defects and the Bartha strain with the restored gIII, gI/gp63 and ORF defects was performed to determine the contribution of these defects to the virulence of PRV in pigs. In this experiment the Bartha strain proved to be non-virulent, the Bartha strain with the restored gIII and gI/gp63 defects proved to be very mildly virulent. The restoration of the ORF resulted in a full virulent PRV strain. Restoration of the other parts of the BamHI-4 fragment did not have any influence on the virulence (FIG. 1).

4. Construction of a Deletion and Insertion in the Open Reading Frame.

To construct an ORF PRV Kaplan mutant, the left 3.8 kb BamHI/SalI fragment of the BamHi-4 was cloned into the multiple cloning site of pBR322. When the left BamHI site was deleted by cleavage with BamHI, Klenow fill up and religation. Cleavage with Bst-XI/StuI resulted in a 126 bp deletion within the ORF. In this deletion an unique BamHI site was created by linker insertion. In this new BamHI site, a gX-βGal expression cassette (Mettenleiter et al., J of Virol Meth., 30, 55–66 (1990)) was inserted. The ORF with the βGal cassette was then used for cotransfection with the PRV Kaplan strain. All blue staining plaques were isolated, checked by restriction analyses and southern blotting, and further purified by three rounds of plaque purification.

I claim:

1. An isolated DNA molecule consisting of a nucleotide sequence encoding the protein shown in SEQ ID NO:2.

2. The DNA molecule of claim 1, consisting of the nucleotide sequence shown in SEQ ID NO:1.

3. A recombinant DNA molecule comprising a DNA sequence that codes for the polypeptide shown in SEQ ID NO: 2, and in which an insertion or deletion mutation is present in the DNA sequence such that functional polypeptide is not produced.

4. A host cell transformed with a recombinant DNA molecule according to claim 3.

5. A method for the preparation of a Pseudorabies Virus (PRV) mutant, comprising introducing an insertion or deletion mutation in the PrV genome in the open reading frame (ORF) that encodes the polypeptide shown in SEG ID NO:2.

6. The method according to claim 5, wherein the mutation is introduced by means of in vivo homologous recombination.

7. The method according to claim 6, wherein a host cell is co-transfected with PrV genomic DNA and a DNA molecule containing the ORF in which the mutation is introduced.

8. The method according to claim 5, wherein the mutation comprises the insertion of a heterologous nucleic acid sequence encoding an antigen of a porcine pathogen.

9. A PrV mutant which comprises a deletion or insertion in an open reading frame encoding a polypeptide shown in SEQ ID NO:2.

10. A vaccine effective in combating infectious disease in pigs, comprising a PRV mutant that has a deletion or insertion mutation in the open reading frame encoding the polypeptide shown in SEQ ID NO:3.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 1578 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Pseudorabies virus
    ( B ) STRAIN: Kaplan ( x i ) SEQUENCE DESCRIPTION: SEQ ID NO:1:

| | | | | | |
|---|---|---|---|---|---|
| ATGGAGTTTG | AGTACCAGAG | CACGATCGTG | CACCAGGGGG | TGCTGTTCTA | CGTCGCCGAC | 60 |
| GGCGGGGACC | GCGCGTACTT | TGTGCACGGG | GGCTGCATCG | TGTCCGTGCA | CCGGCGCTCG | 120 |
| CGGGAGATCG | GCAAGTTCGG | GCTCACGCTG | CGCGGGAACG | CGCCCGGGAA | CCGCGTCGTC | 180 |
| GCCAACTACG | TGCGCACGGA | GCTGGCGCGC | CTCGGCCGCG | CGTGGGCCGC | CCCGCAGGGG | 240 |
| AGCGACGACG | TCTTCGTGGA | CGCCCTGGGG | CTGCTGCTGC | CGCTGACGGA | GCTGGACCTC | 300 |
| TGCGGCCGCG | CGGAGCTGGA | CGTGTACGAC | CCCTACCTCG | TCGAGTGCAT | GGTCTCGCTG | 360 |
| CCGGCGTCGG | CGCTCTCGCT | GACGCTCGTG | CACGACCGCC | AGCAGGACCG | CGTCCTGGAG | 420 |
| CTCCTGGCCG | AGCCCGCCAT | CGTGCACCCC | TCCTCGGGCT | TCGTGTACGC | CGTGAACGAG | 480 |
| GCCTGCTTCG | CGCTGGTGCA | GGCGTACCTC | TCCGAGCTGC | CCAGCTCGCT | GCAGGTGCTG | 540 |
| ACGGAGGGGC | TCTTTGACGG | CATCCCCGGC | GTGCGCCCCC | CGCTCAGCGG | CGAGACGCGG | 600 |
| CCCACGGCCG | TGGTGGTGAA | GGGCGGGCGC | GCGGCCCCCA | CGCTGAGCGT | GCGCCCGCGC | 660 |
| CGGTACGCCG | AGCGCGCGCT | GCGCGCGACG | GTGGTCAGCG | ACTTTGTGCA | GGTGCGCTAC | 720 |
| ATCCCGGCGA | CGCGGCGCAT | CTGGGCGACG | CGCGGCGGGA | GCCTGTCCCT | GCAGATGCTC | 780 |
| TGCGACCTCG | TGGCCGGGGC | GGACGCCATC | CTGCGGCGGG | CCGCGGGCGC | CTCGGACGAC | 840 |
| GCCTCGGCCG | CCGTGGTCGA | GGCCGTGTCC | GCCGTCGCGG | CGGACCCCTT | CTTCGGGACG | 900 |
| GGCTCCACGT | CGCTCACGGG | CGCGCAGCGG | TTCGCGCTGT | ACCAGTTCAT | CCTGGCCCGC | 960 |
| TGGCACCTGC | CGAGCTGCTA | CGCCGCGCTG | GAGGGCATGC | TCGACAGGCT | GGACGAGCGC | 1020 |
| CCCGGGGCGG | GCGCGGGCGA | CGACGACGAC | GACGACGGAG | GAGAAGGGGG | AGGAGGGGGC | 1080 |
| GGCCACGGCG | GCTCTCGGGC | CGCGAGCGCC | GTGGCCCACG | CCGTCAACCG | CGTGCTGCGC | 1140 |
| GAGGCGACCG | TCTTCGGCGA | GGTGATGCGG | ATGCTCGTGA | ACGCCGCCGT | GGTGCACGCC | 1200 |
| CCCGCGATCG | CGGACCCGGC | GGGGGCCTCG | CCGCCGACGA | CGAAGCACGC | CCGGGAGGAC | 1260 |
| GCGGCGACGG | GCCTGGAGCT | GGCGGTCATG | ATGAGCGACG | CGGAGACGAA | CGCGCCGGAC | 1320 |
| GCCGACGCGT | GCGAGCTGGT | GGAGGCGGCC | GGGGCGCGGG | TGCTGGACGG | GCTCTACGCC | 1380 |
| GGCCGGGGCC | TCGTCGCCGC | GACGGCGCCC | GTGGGCGCG | CGCTGCGGCC | CACGTCCGCC | 1440 |
| GTCTGCGCCG | AGGCGGCGCT | CCTGACCGCC | TTCGGCGACT | CGCCCGCGGC | CCTCCGCGGG | 1500 |
| GCCCAGTACC | TGTTTCAGCT | GTTTCGGGCG | CGCCTGACCC | GCGCCAACAT | CTCCATCGTC | 1560 |
| CTCAATAAAA | ACCGTTAA | | | | | 1578 |

( 2 ) INFORMATION FOR SEQ ID NO:2:

( i ) SEQUENCE CHARACTERISTICS:
        ( A ) LENGTH: 525 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:

(A) ORGANISM: Pseudorabies virus
(B) STRAIN: Kaplan (xi) SEQUENCE DESCRIPTION: SEQ ID NO:2:

| | | | | | | | | | | | | | | |
|---|---|---|---|---|---|---|---|---|---|---|---|---|---|---|
| Met 1 | Glu | Phe | Glu | Tyr 5 | Gln | Ser | Thr | Ile | Val 10 | His | Gln | Gly | Val | Leu Phe 15 |
| Tyr | Val | Ala | Asp 20 | Gly | Gly | Asp | Arg | Ala 25 | Tyr | Phe | Val | His | Gly 30 | Gly Cys |
| Ile | Val | Ser 35 | Val | His | Arg | Arg | Ser 40 | Arg | Glu | Ile | Gly | Lys 45 | Phe | Gly Leu |
| Thr | Leu 50 | Arg | Gly | Asn | Ala | Pro 55 | Gly | Asn | Arg | Val | Val 60 | Ala | Asn | Tyr Val |
| Arg 65 | Thr | Glu | Leu | Ala | Arg 70 | Leu | Gly | Arg | Ala | Trp 75 | Ala | Ala | Pro | Gln Gly 80 |
| Ser | Asp | Asp | Val | Phe 85 | Val | Asp | Ala | Leu | Gly 90 | Leu | Leu | Leu | Pro 95 | Leu Thr |
| Glu | Leu | Asp | Leu 100 | Cys | Gly | Arg | Ala | Glu 105 | Leu | Asp | Val | Tyr | Asp 110 | Pro Tyr |
| Leu | Val | Glu 115 | Cys | Met | Val | Ser | Leu 120 | Pro | Ala | Ser | Ala | Leu 125 | Ser | Leu Thr |
| Leu | Val 130 | His | Asp | Arg | Gln | Gln 135 | Asp | Arg | Val | Leu | Glu 140 | Leu | Leu | Ala Glu |
| Pro 145 | Ala | Ile | Val | His | Pro 150 | Ser | Ser | Gly | Phe | Val 155 | Tyr | Ala | Val | Asn Glu 160 |
| Ala | Cys | Phe | Ala | Leu 165 | Val | Gln | Ala | Tyr | Leu 170 | Ser | Glu | Leu | Pro 175 | Ser Ser |
| Leu | Gln | Val | Leu 180 | Thr | Glu | Gly | Leu | Phe 185 | Asp | Gly | Ile | Pro | Gly 190 | Val Arg |
| Pro | Pro | Leu 195 | Ser | Gly | Glu | Thr | Arg 200 | Pro | Thr | Ala | Val | Val 205 | Lys | Gly |
| Gly | Arg 210 | Ala | Ala | Pro | Thr | Leu 215 | Ser | Val | Arg | Pro | Arg 220 | Arg | Tyr | Ala Glu |
| Arg 225 | Ala | Leu | Arg | Ala | Thr 230 | Val | Val | Ser | Asp | Phe 235 | Val | Gln | Val | Arg Tyr 240 |
| Ile | Pro | Ala | Thr | Arg 245 | Arg | Ile | Trp | Ala | Thr 250 | Arg | Gly | Gly | Ser | Leu Ser 255 |
| Leu | Gln | Met | Leu 260 | Cys | Asp | Leu | Val | Ala 265 | Gly | Ala | Asp | Ala | Ile 270 | Leu Arg |
| Arg | Ala | Ala 275 | Gly | Ala | Ser | Asp | Asp 280 | Ala | Ser | Ala | Ala | Val 285 | Val | Glu Ala |
| Val | Ser 290 | Ala | Val | Ala | Ala | Asp 295 | Pro | Phe | Phe | Gly | Thr 300 | Gly | Ser | Thr Ser |
| Leu 305 | Thr | Gly | Ala | Gln | Arg 310 | Phe | Ala | Leu | Tyr | Gln 315 | Phe | Ile | Leu | Ala Arg 320 |
| Trp | His | Leu | Pro | Ser 325 | Cys | Tyr | Ala | Ala | Leu 330 | Glu | Gly | Met | Leu | Asp Arg 335 |
| Leu | Asp | Glu | Arg 340 | Pro | Gly | Ala | Gly | Ala 345 | Gly | Asp | Asp | Asp | Asp 350 | Asp Asp |
| Gly | Gly | Glu 355 | Gly | Gly | Gly | Gly | Gly 360 | Gly | His | Gly | Gly | Ser 365 | Arg | Ala Ala |
| Ser | Ala 370 | Val | Ala | His | Ala | Val 375 | Asn | Arg | Val | Leu | Arg 380 | Glu | Ala | Thr Val |
| Phe 385 | Gly | Glu | Val | Met | Arg 390 | Met | Leu | Val | Asn | Ala 395 | Ala | Val | Val | His Ala 400 |

| | | | | | | | | | | | | | | |
|---|---|---|---|---|---|---|---|---|---|---|---|---|---|---|
| Pro | Ala | Ile | Ala | Asp 405 | Pro | Ala | Gly | Ala | Ser 410 | Pro | Pro | Thr | Thr | Lys 415 | His |
| Ala | Arg | Glu | Asp 420 | Ala | Ala | Thr | Gly | Leu 425 | Glu | Leu | Ala | Val | Met 430 | Met | Ser |
| Asp | Ala | Glu 435 | Thr | Asn | Ala | Pro | Asp 440 | Ala | Asp | Ala | Cys | Glu 445 | Leu | Val | Glu |
| Ala | Ala 450 | Gly | Ala | Arg | Val | Leu 455 | Asp | Gly | Leu | Tyr | Ala 460 | Gly | Arg | Gly | Leu |
| Val 465 | Ala | Ala | Thr | Ala | Pro 470 | Val | Gly | Arg | Ala | Leu 475 | Arg | Pro | Thr | Ser | Ala 480 |
| Val | Cys | Ala | Glu | Ala 485 | Ala | Leu | Leu | Thr | Ala 490 | Phe | Gly | Asp | Ser | Pro 495 | Ala |
| Ala | Leu | Arg | Gly 500 | Ala | Gln | Tyr | Leu | Phe 505 | Gln | Leu | Phe | Arg | Ala 510 | Arg | Leu |
| Thr | Arg | Ala 515 | Asn | Ile | Ser | Ile | Val 520 | Leu | Asn | Lys | Asn | Arg 525 | | | |